(12) United States Patent
Guerrero

(10) Patent No.: US 10,874,756 B1
(45) Date of Patent: Dec. 29, 2020

(54) SANITIZING CABINET ASSEMBLY AND METHOD OF OPERATION

(71) Applicant: ODY International LLC, Las Vegas, NV (US)

(72) Inventor: Ulises Guerrero, Las Vegas, NV (US)

(73) Assignee: Envirody Inc., Las Vegas, NV (US)

( * ) Notice: Subject to any disclaimer, the term of this patent is extended or adjusted under 35 U.S.C. 154(b) by 0 days.

(21) Appl. No.: 16/793,328

(22) Filed: Feb. 18, 2020

Related U.S. Application Data

(60) Provisional application No. 62/912,632, filed on Oct. 8, 2019.

(51) Int. Cl.
*A61L 2/20* (2006.01)
*A61L 2/10* (2006.01)
*A61L 2/28* (2006.01)

(52) U.S. Cl.
CPC ............... *A61L 2/202* (2013.01); *A61L 2/10* (2013.01); *A61L 2/28* (2013.01); *A61L 2202/121* (2013.01); *A61L 2202/122* (2013.01); *A61L 2202/14* (2013.01); *A61L 2202/15* (2013.01)

(58) Field of Classification Search
None
See application file for complete search history.

(56) References Cited

U.S. PATENT DOCUMENTS

| | | | | |
|---|---|---|---|---|
| 3,117,832 A | * | 1/1964 | Thomas | A61L 2/206 422/23 |
| 2014/0193294 A1 | * | 7/2014 | Kain | A61L 2/202 422/3 |
| 2018/0104369 A1 | * | 4/2018 | Watanabe | A61L 2/202 |

FOREIGN PATENT DOCUMENTS

CN         202636113 U   *   1/2013

OTHER PUBLICATIONS

English machine translation of CN 202636113 U entitled Multi-functional storage cabinet provided by Proquest (Year: 2013).*

* cited by examiner

*Primary Examiner* — Holly Kipouros
(74) *Attorney, Agent, or Firm* — Michael D. Eisenberg

(57) ABSTRACT

A cabinet provides a continuous sanitizing environment for items contained within the cabinet. The sanitizing environment is achieved by generated oxygen, ozone, and ultraviolet light within the cabinet. Expelled oxygen and ozone from the cabinet sanitize the ambient environment in which cabinet resides in.

20 Claims, 8 Drawing Sheets

114

112

SANITIZING CABINET ASSEMBLY AND METHOD OF OPERATION

CROSS-REFERENCES TO RELATED APPLICATIONS

This application claims priority from U.S. Provisional Application Ser. No. 62/912,632 filed Oct. 8, 2019, which is hereby incorporated herein by reference in the respective in its entirety.

TECHNICAL FIELD

This invention relates to sanitizing of objects.

BACKGROUND OF THE INVENTION

In many instances, hospitals, clinics, and medical emergency sites have in place important infection control. Typically, hand sanitizing stations and mobile isolation units are currently available in the infection prevention and control industry.

It is often necessary to provide a plurality of items of cutlery and food preparation implements such as knives of various sizes and blade configurations. Such an assortment of items are desirable in the kitchen and particularly in installations such as meat markets, butcher shops, restaurants and the like wherein continuous cutting and preparing operations take place.

In supermarkets, butcher shops, and restaurants, where meat is being continuously prepared for consumption, a wide variety of cutlery is generally provided such as trimming and slicing knives. It is also highly desirable that the kitchen cutlery, which is in constant use, be kept in a well sharpened and clean condition in order to facilitate efficient and sanitary cutting operations.

BRIEF SUMMARY OF EMBODIMENTS OF THE INVENTION

According to one embodiment of the invention, a sanitation cabinet is disclosed. The sanitation cabinet can include: a hollow housing for storing one or more objects, the housing having a back wall, a front door opposite the back wall, a first side wall, a second side wall opposite the first side wall, a lower floor panel and a ceiling panel, the floor panel having an intake vent configured for intake of air from an external environment into an inner cavity of the housing, and the ceiling panel having an exhaust vent configured to exhaust air from the inner cavity of the housing to the external environment; at least one fan located on or near the floor panel and configured to generate an air flow from the outside environment into the inner cavity through the intake vent and back out into the outside environment via the exhaust vent; an ozone generator located on or near the floor panel and configured to generate ozone from at least some of the air entering via the intake vent; an oxygen generator located on or near the floor panel and configured to generate oxygen from at least some of the air entering via the intake vent; at least one ultra-violet lamp joined to at least one of the first side wall and the second side wall, and the at least one ultra-violet lamp facing the inner cavity and configured to generate ultra-violet light propagating within the inner cavity to sanitize the inner cavity; an air analyzer located in the inner cavity and configured to sample air in the inner cavity to identify a presence of one or more predetermined microbes and to generate data indicative of the presence of the one or more predetermined microbes; a control unit, configured for receiving the data from the air analyzer and to activate the fan and at least one of the ozone generator, the oxygen generator, and the ultra-violet lamp according to a predetermined schedule in order to kill at least a portion of the microbes identified by the air analyzer.

According to another embodiment, the sanitation cabinet can include at least one transparent shelf configured to hold the one or more objects and allowing transmission of the ultra-violet light through the shelf onto the one or more objects.

According to another embodiment, the sanitation cabinet can include the at least one ultra-violet lamp comprises a first ultra-violet lamp joined to the first side wall; and the first side wall comprises a first hinged side door opening outwards, the first ultra-violet lamp being joined to the first side door.

According to another embodiment, the sanitation cabinet can include the at least one ultra-violet lamp comprises a second ultra-violet lamp joined to the second side wall; and the second side wall comprises a second hinged side door opening outwards, the second ultra-violet lamp being joined to the second side door.

According to another embodiment, an inward-facing surface of the inner cavity comprises is reflective to ultra-violet light.

According to another embodiment, the at least one ultra-violet lamp comprises: a first ultra-violet lamp joined to the first side wall; a second ultra-violet lamp joined to the second side wall; and a third ultra-violet lamp joined to the ceiling panel.

According to another embodiment, the at least one ultra-violet lamp comprises a wand which is repeatedly detachable from the hollow housing.

According to another embodiment, the wand comprises: a light source, for emitting the ultra-violet light; and a rechargeable power source; wherein the hollow housing comprises a charging station configured for charging the power source when the wand is joined to the hollow housing.

According to another embodiment, the control unit comprises a user interface configured to: receive an input from a user indicative of an instruction to operate at least one of the ozone generator, the oxygen generator, and the at least one ultra-violet lamp, according to an operation mode; and operate at least one of the ozone generator, the oxygen generator, and the at least one ultra-violet lamp, according to the input.

According to another embodiment, the control unit comprises an output interface configured to display information showing whether the operation of the at least one of the ozone generator, the oxygen generator, and the ultra-violet lamp is in progress.

According to another embodiment, an automatic lock on the front door, the control unit being configured to engage the automatic lock to lock the front door when the operation of the ozone generator is in progress and to disengage the automatic lock to unlock the front door when the operation of the ozone generator ends.

According to another embodiment, the sanitation cabinet can include an inner floor panel located above the floor panel and having a second vent; wherein the ozone generator and the oxygen generator are located between the inner floor panel and the lower floor panel, such that the ozone generated by the ozone generator and the oxygen generated by the oxygen generator are driven into the inner cavity via the second vent.

According to another embodiment, the exhausted vent is configured to be opened and closed.

According to another embodiment, the control unit is configured to control an opening and closing of the exhaust vent.

In some embodiments of the present invention, the sanitation cabinet further comprises an ozone removal filter and an ozone removal fan. The ozone removal filter is located in the inner cavity and is configured to remove ozone from air flowing therethrough. The ozone removal fan is located in the inner cavity in a vicinity of the ozone removal filter and is configured to drive air in the inner cavity through the ozone removal filter. The user interface is configured to receive an interruption input indicative of an instruction to interrupt the predetermined schedule. Responsive to the interruption input, the control unit is configured to activate the ozone removal fan to drive the air in the inner cavity through the ozone removal filter.

In a variant, the control unit is configured to turn off the ozone removal fan when the control unit has determined that an ozone level in the inner cavity is below a predetermined safe level.

In another variant, the control unit is configured to determine that the ozone level in the inner cavity is below the predetermined safe level if the ozone removal fan has operated for a predetermined time period.

In yet another variant, the air analyzer is further configured to measure the ozone level in the inner cavity, to generate ozone measurement data indicative of the ozone level measured by the air analyzer, and to transmit the ozone measurement data to the control unit. The control unit is configured to determine that the ozone level in the inner cavity is below the predetermined safe level by comparing the ozone level measured by the air analyzer to the predetermined safe level and determining that the ozone level measured by the air analyzer is below the predetermined safe level.

In a further variant, the sanitation cabinet includes an automatic lock on the front door. The control unit is configured to engage the automatic lock to lock the front door when the operation of the ozone generator or the oxygen generator or the ultra-violet lamp is in progress and to disengage the automatic lock to unlock the front door when the operation of the ozone generator or the oxygen generator or the ultra-violet lamp ends. The control unit is configured to disengage the automatic lock when the control unit has determined that the ozone level in the inner cavity is below the predetermined safe level.

In yet a further variant, the ozone removal filter is closed and the control unit is configured to open the ozone removal filter for air to be driven through the ozone removal filter in response to the interruption input.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
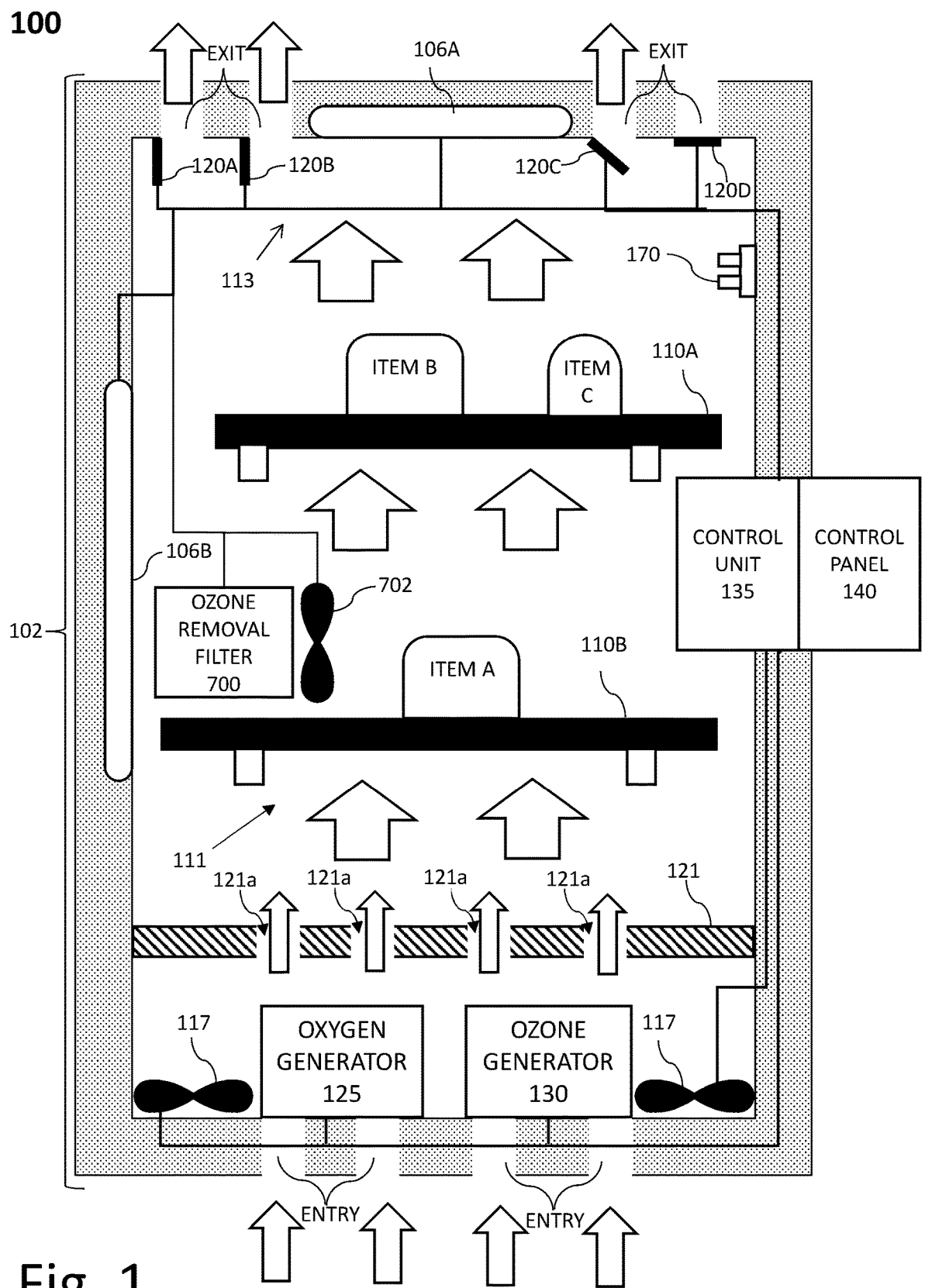
FIG. 1 is a schematic drawing illustrating a sanitizing cabinet assembly, in accordance with some embodiments of the present invention.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

The present invention is directed toward a combination UV, oxygen, and ozone sanitizing cabinet (Assembly 100) and methods of operation of the sanitizing cabinet.

Referring to the figures, the sanitizing cabinet assembly 100, hereafter "assembly 100" provides a housing 102 configured to sanitize items contained therein. These items can be, but are not limited to, medical instruments, medicine, food preparation equipment, toys, biologics, perishable materials, and other items that may require thorough sanitizing prior to use. Additionally, assembly 100 provides a continuous sanitizing environment for the items contained therein. Glove boxes and fumigation hoods can provide some level of sanitization, but require frequent maintenance and can be corrupted by oxygen ($O_2$), ozone ($O_3$), ultraviolet (UV) light, hydrogen sulfide ($H_2S$) gas, hydrogen chloride (HCl) vapor, oxidizers, chlorinated solvents, and dust.

Referring to FIGS. 1-8, assembly 100 comprises a housing 102 defined by a back wall 113, sidewalls 115, a ceiling panel 114, and a lower floor panel 112. The walls have respective outer and inner surfaces. In some embodiments, at least the ceiling panel 114 and the lower floor panel 112 have vents and apertures therein. The assembly 100 also includes at least one front door opposite the back wall configured to be opened and closed in order to open and close the front of the housing 102. In some embodiments of the present invention, two front doors 108A and 108B are present and are configured to cooperate with each other to close the front of the housing 102.

An outer perimeter of housing 102, as depicted by the shaded pattern in FIG. 1, may be constructed of metal alloys. Doors 108A and 108B are connected to the right side wall of the outer perimeter and the left side wall of the outer perimeter, respectively. The bottom apertures denoted as "Entry" of the outer perimeter are configured for funneling air from the ambient environment into housing 102, where at least some air interacts with the oxygen generator 125 and at least some air interacts with the ozone generator 130. Oxygen generator 125 generates and expels oxygen, which is derived from the air as entered into the bottom apertures. Ozone generator 130 generates and expels ozone, which is derived from the air as entered into the bottom apertures. One or more fans 117 drive air from the apertures in the lower floor panel 112 and spread oxygen and ozone in an upwards direction toward shelves 110A-B and the vents of ceiling panel 114. The lower floor panel 112 contains entry apertures. The oxygen generator 125, ozone generator 130, fan(s) 117 are located near or on the lower floor panel 112. In some embodiments of the present invention, the assembly 100 includes an inner floor panel 121 located above the lower floor panel 112 and having one or more second apertures 115*a*. The ozone generator 130 and the oxygen generator 125 are located between the inner floor panel 121 and the lower floor panel 112, such that the ozone generated by the ozone generator and the oxygen generated by the oxygen generator are driven into the inner cavity of the housing via the second apertures 115*a*. The space between the lower floor panel and the inner floor panel 121 provides an enclosure to protect to the oxygen generator 125, the ozone generator 130, and the fan(s) 117.

The back wall 113 is attached to the side walls 115, lower floor panel 112, and ceiling panel 114. The inner cavity of the housing is enclosed by the back wall 112, the side walls 115, the ceiling panel 114, the lower floor panel 112, and the front door(s) 108A-B. Shelves 110A-B are attached to back wall 113 and/or the side walls 115 and contained within the cavity. Vents, as denoted by "Exit", in ceiling panel 114 expel air, oxygen, and ozone from cabinet 102. In some embodiments of the present invention, vent doors 120A-D are attached to the vents denoted by "Exit" for controlling the rate of expelling oxygen and ozone from cabinet 100.

Ultraviolet (UV) lamps 106A, 106B, and 106C are designed to propagating UV light towards the items on the shelves 110A-B and are located in the inner cavity. In some embodiments of the present invention, at least one UV lamps is included in the assembly 100 and is joined to one of the side walls 115. If more than one UV lamp is present, the other UV lamps may be joined to the ceiling panel 114 or more side walls 115. Wiring 113, which is connected to control unit 135, sends electrical commands to control the functioning of vent doors 120A-B, oxygen generator 125, ozone generator 130, fan(s) 117, and UV lamps 106A-C.

Cabinet 102 can be made mobile by attaching removable wheels to the bottom wall (i.e., the surface containing apertures where air from ambient environment can enter into). The apertures where air can enter through are denoted as "Entry" and allow air to reach the oxygen generator 125 and the ozone generator 130. The assembled version of cabinet 102 can have heavy-duty legs for stability with the option of having locking wheels.

In one embodiment, a panel containing an oxygen generator 125 and ozone generator 130 are located in a bottom of cabinet 102, near or on the lower floor panel. Gas filtration and separation systems reside within oxygen generator 125 to separate nitrogen and other gases from oxygen. Optionally, the oxygen is further subjected to drying pellets in oxygen generator 125 to obtain purified and dry oxygen. The purified and optionally dried oxygen is expelled from oxygen generator 125. Gas filtration and separation systems reside within ozone generator 125 to separate nitrogen and other gases from oxygen. Optionally, the oxygen is further subjected to drying pellets in ozone generator 130 to obtain purified and dry oxygen. The oxygen is subjected to high pressures and/or is irradiated with UV light to obtain ozone. The purified ozone is expelled from ozone generator.

Special care must be taken with the materials used to construct oxygen generator 125, ozone generator 130, fan(s) 117, shelves 110A-B, and doors 108A-B. For example, copper and iron can be oxidized to cupric oxide and ferric oxide, respectively. Metal alloys, plastics, silicone, glasses (i.e., silicates), and rubber can be used as the materials for constructing construct UV lamps 106A-C, generator 125, ozone generator 130, fan(s) 117, shelves 110A-B, and doors 108A-B.

UV lamps 106A-C radiate high energy UV-C light for significantly reducing microscopic germs, mold and dust mites. In some embodiments of the present invention, an upper UV lamp 106A resides in top wall 114, a left UV lamp is located in the left side wall 115, and a right UV lamp resides in the right side wall 115.

Control panel 140 is located to the cabinet 102 and faces outward, to enable access to a user located outside the cabinet. Control panel 140 is electrically connected to control unit 135, which is connected to wiring 113. Thus, control panel 140 is a digital interface where a user can enter commands for controlling the operation of the assembly 100. Example of operation parameters that may be controlled by the user include: time delays and run times for UV irradiation and the expulsion of ozone and oxygen from ozone generator 130 and oxygen generator 125; a pre-clean cycle, cleaning cycle, a post clean cycle can also be programmed to sanitize items A-C and shelves 110-B. The cycle in progress and cycle completed LEDs are displayed on the front of control panel 140 with a start timer and stop cycle timer push button.

Wiring 113 transports commands from the control unit 135 to control one or more of: (i) the positions of vent doors 120A-D to control the amount of oxygen and ozone expelled from cabinet 102 to the ambient atmosphere; (ii) the amount of, rate of, and timing of oxygen expulsion from oxygen generator 125; (iii) the amount of, rate of, and timing of ozone expulsion from ozone generator 130; (iv) the speed of and timing of operating the blades of fan(s) 117 to cause air flow into the cabinet 102 through the bottom apertures in the lower floor panel 112 and to cause the spread the oxygen and ozone upwards towards shelves 110A-B and out of the cabinet via the vents in the ceiling panel 114; and (v) the amount of, rate of, and timing of UV radiation from UV lamps 106A-C.

As depicted in FIG. 1, vent doors 120A-120B are oriented at 90 degrees with respect to the ceiling panel (i.e., a completely opened position) and thereby the expulsion of oxygen and ozone from cabinet 102 is not blocked through the left two vents. Vent door 120C is oriented 45 degrees respect to the ceiling panel (i.e., a partially closed position) and thereby the expulsion of oxygen and ozone is partially blocked through the second rightmost vent. Vent door 120D is oriented 0 degrees respect to the ceiling panel (i.e., a completely closed position) and thereby the expulsion of oxygen and ozone is completely blocked through the rightmost vent.

In one non-limiting embodiment, all contents in the cavity of the cabinet 102 are 99.98% free of contaminants and germs and at a safe level of ozone, as confirmed by laboratory tests conducted by the inventor. More specifically, control unit 135 via control panel 140 can be programmed to control the relative proportion of oxygen expelled from oxygen generator 125 to ozone expelled from ozone generator 130, such that the proportion of oxygen is much greater than ozone. Thus, the concentration of ozone is substantially diluted in cabinet 102 and the concentration of oxygen is substantially increased in cabinet 102 to destroy or aid in destroying microorganisms needed for sanitizing the items (i.e. items A-C) and the components of cabinet 102 without destroying or damaging the structural integrity of containers storing items A-C and the components of cabinet 102. In one non-limiting embodiment, the assembly 100 contains three UV lamps to sanitize the items contained inside cabinet 102. One or more of the three lights can be a removable wand.

The items in the cabinet 112 can be sanitized by exposure to one or more of the following: (i) UV light from UV lamps (i.e., lamps 106A-C) inside cabinet 102; (ii) ozone that is generated by generator 125; and (iii) oxygen that is generated by generator 130. In doing so, the items A-C and other contents inside cabinet 102 are exposed to the combination of UV light, oxygen, and ozone. Microorganisms (e.g., bacteria and algae) residing on metal, plastic, wood, glass, or moistened surfaces of items A-C and shelves 110A-B which can cause food poisoning and/or contamination are killed by the combination of UV light, oxygen, and ozone. Thus, the combination facilitates chemical-free sanitization within the continuous sanitizing environment of assembly 100.

Figure 8:
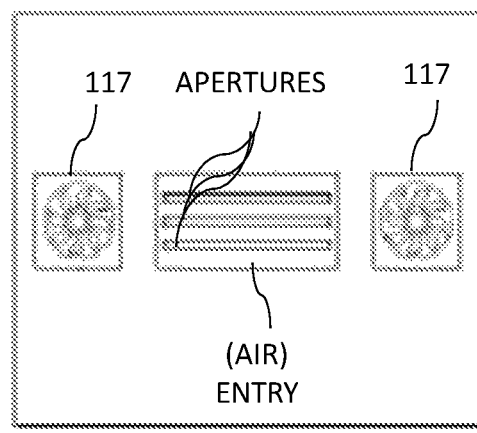
FIG. 8 is a top view of the lower floor panel of the cabinet, according to some embodiments of the present invention.

In addition to sanitizing the contents inside the cabinet 102, the assembly 100 also sanitizes the ambient air in that room cabinet 102 sits in (e.g., a 900 square foot space). More specifically, vents in the top wall 114 of cabinet 102 expel ozone and oxygen gases from cabinet 102 for external sanitization functions (FIG. 8). In some embodiments of the present invention, the assembly 100 is provided in at least three different sizes of cabinet 102, and thereby accommodates different items and sanitizing requirements. The assembly 100, which provides continuous sanitizing for the items contained therein and sanitization in the ambient air in the room can create a clean environment across different settings (e.g., schools, medical clinics, gyms, fire departments, the food industry, and chemical processing), by exhausting oxygen and/or ozone into an environment outside the cabinet. Stated another way, the clean environment due to sanitization is not limited to the contents inside cabinet 102. Furthermore, if there are multiple cabinets in a building the cabinets can be programmed to operate overnight when the building is empty in different locations in the building and sanitize the building from mold, germs, and unwanted odors.

In some embodiments of the present invention, the control unit 135 stores a plurality of predetermined operation modes, and the control panel 140 includes an input unit (such as a touchscreen, a keypad, buttons, etc.), which is configured to receive from the user a selection of one of the operation modes. The control unit 135 is configured to receive the user's selection and to operate the oxygen generator 125, and/or the ozone generator 130, and/or the fan(s) 117, and/or one or more of the UV lamps, and/or one of the vent doors 120A-D (if present), according to the user's selected operation mode.

In some embodiments of the present invention, the assembly 100 includes an air analyzer sensor 170 located in the inner cavity and configured to sample air in the inner cavity to identify a presence of one or more predetermined microbes and to generate data indicative of the presence of the one or more predetermined microbes. The control unit is configured to receive the data from the air analyzer sensor and to activate the fan and at least one of the ozone generator, the oxygen generator, and the ultra-violet lamp(s) according to a predetermined schedule (operation mode) configured to kill at least a portion of the microbes identified by the air analyzer.

In some embodiments of the present invention, the assembly 100 further includes an ozone removal filter 700 and an ozone removal fan 702. If ozone removal filter 700 is configured to remove ozone from air driven therethrough via the ozone removal fan 702. For example, if the assembly 700 is turned off before the end of a sanitation cycle, the ozone level inside the inner cavity may be higher than a desirable amount (e.g. higher than a safe amount that can be inhaled by a person), and it may be unsafe to open the door(s). Thus, when a sanitation cycle is interrupted, the ozone removal fan 702 is activated by the control unit 135 to drive air to the ozone removal filter 700, and the ozone removal filter 700 is opened by the control unit 135 to receive the air driven by the ozone removal fan 702. Once enough ozone has been filtered by the ozone removal filter 700 and the ozone level has been reduced to a safe predetermined level, it is safe to open the door(s). The ozone removal filter may include, for example charcoal, or any other material that is known to retain or break down ozone. In some embodiments of the present invention, the door(s) are kept locked until the control unit 135 determines that ozone level has fallen below the safe level. In some embodiments of the present invention, the ozone removal filter 700 remains closed during the normal operation of the assembly 700, when ozone is needed to sanitize the items in the cavity or is exhausted from the exhaust vents to sanitize a room. In this manner, air laden with ozone is prevented from entering the ozone removal filter and from losing the ozone in the ozone removal filter. The ozone removal filter 700 is opened if a sanitation cycle is interrupted and/or at the end of a sanitation cycle, when ozone is no longer needed and needs to be removed from the inner cavity in order to enable a user to safely open the door(s).

In some embodiments of the present invention, after the ozone removal fan 702 has operated for a predetermined time period and driven air through the ozone removal filter 700, it is assumed that the ozone level has fallen to a safe predetermined level. The time period is determined experimentally in the development phase of the assembly 100. In some embodiments of the present invention, the air analyzer sensor 170 is further configured to measure the concentration of ozone (also referred to as "ozone level") in the air within the inner cavity. The air analyzer sensor 170 transmits the measured ozone level to the control unit 135. When the ozone level falls below the predetermined safe level, the control unit determines that it is safe to open the doors.

Figure 9:
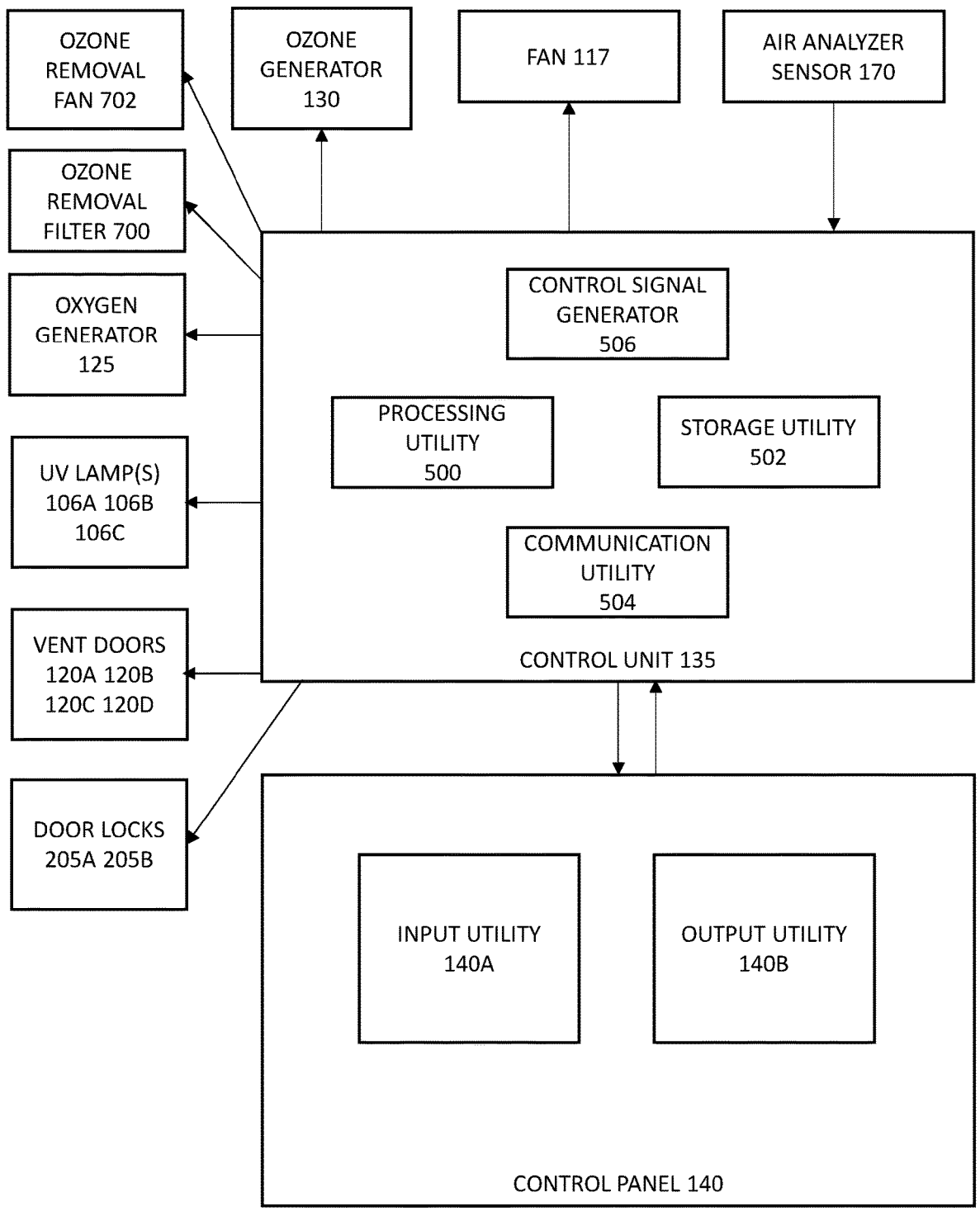
FIG. 9 is a block diagram illustrating communication between the control unit, the control panel, and the elements of the cabinet that are controlled by the control unit, according to some embodiments of the present invention.

FIG. 9 is a block diagram illustrating the control unit 135 and the control panel, according to some embodiments of the present invention.

The control panel 140 includes an input utility 140A and an output utility 140B. The control unit 140 is in wired or wireless communication with the control unit 135, and is configured to send the control unit user inputs and receive from the control unit outputs to be conveyed to the user. The input utility 140A includes software and/or hardware components configured to receive an input from a user. The input from the user may be a selection of an operation mode, an instruction to start the operation of the assembly 100 of FIG. 1, or an instruction to stop the operation of the assembly 100. The input utility 140A may include one or more buttons, a keypad, a touch screen, or a communication device (such as a smartphone, tablet, or computer) which stores computer readable media configured to cause the communication device to receive the input. The output utility 140B is configured to output information to the user, such as the currently selected operation mode and information about the selected operation mode, the time remaining to complete a sanitizing cycle, a notification that the assembly 100 is operating, an error message, a notification that the assembly 100 is not operating, a notification that it is safe to open the door(s). The output utility 140B may include a display, one or more lights of different colors, a speaker, a haptic device.

The control unit 135 includes a processing utility 500, a storage utility 502, a communication utility 504, and a control signal generator 506.

The communication utility 504 is configured enable wired or wireless communication between the control unit 135 and the control panel 140. The storage utility 502 is configured to store machine readable data, which instruct the processing utility 500 to process incoming data from the air analyzer sensor 170 and user inputs received via the control panel and to determine operation modes for the fan(s) 117, the ozone generator 130, the oxygen generator 125, the one or more UV lamps (106A-C), the one or more vent locks (120A-D) if present, the door locks (205A-B) if present, and the ozone removal fan 702 and the ozone removal filter 700 if present. The control signal generator 506 is configured to receive the operation modes determined by the processor and to generate respective control signals accordingly. The control signals are sent to the fan(s) 117, the ozone generator 130, the oxygen generator 125, the one or more UV lamps (106A-C), the one or more vent locks (120A-D) if present, the door locks (205A-B) if present, and the ozone removal fan 702 and the ozone removal filter 700 if present. Responsive to the control signals, the fan(s) 117, the ozone generator 130, the oxygen generator 125, the one or more UV lamps (106A-C), the one or more vent locks (120A-D) if present, the door locks (205A-B) if present, and the ozone removal fan 702 and the ozone removal filter 700, if present, operate according to the operation modes.

Figure 2:
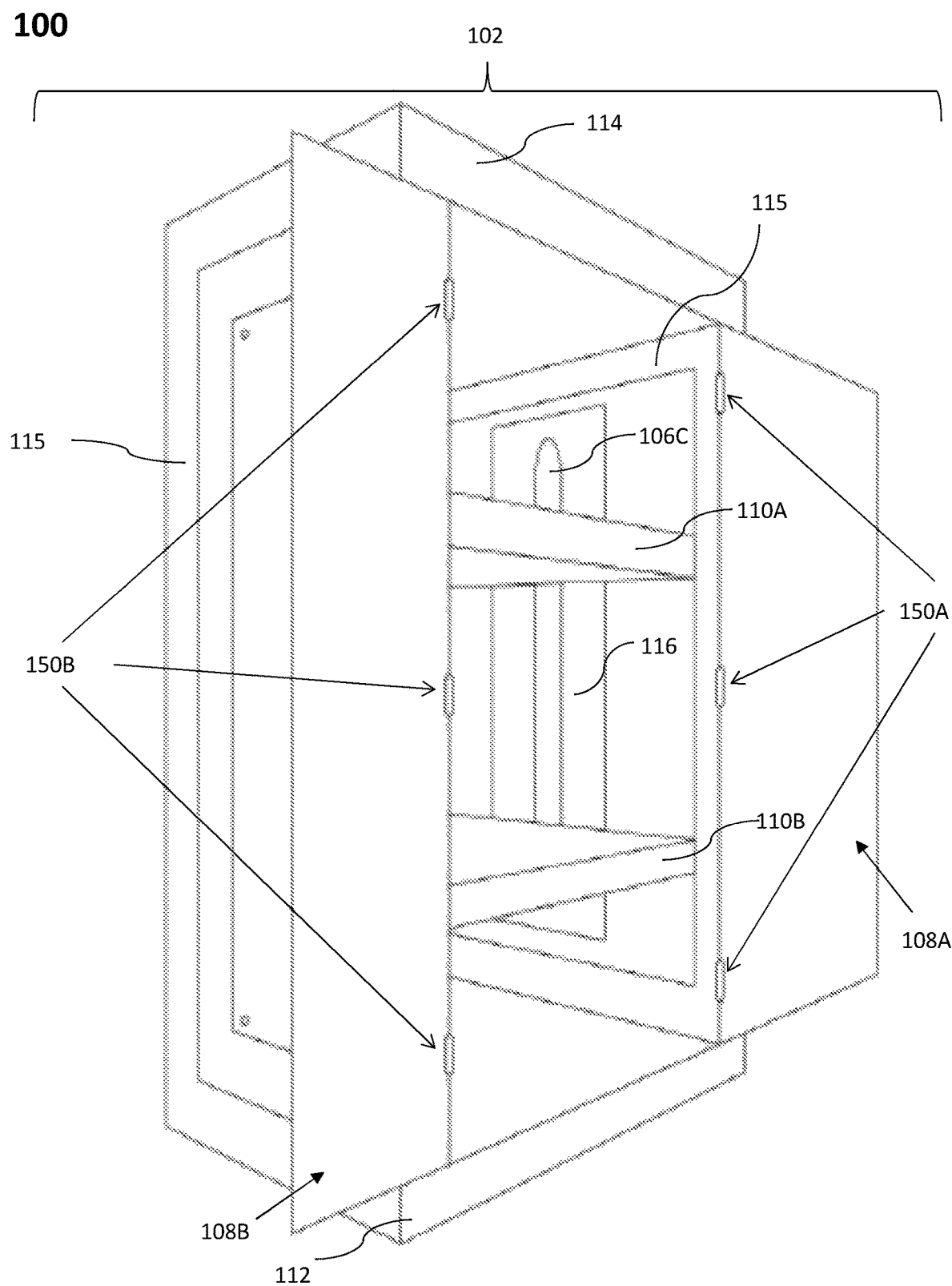
FIG. 2 is an illustration of a perspective view of the assembly, in accordance with some embodiments of the present invention.

Referring to FIG. 2, items A-C are loaded into the cavity of the cabinet 102 where shelves, hooks, and smaller lockers may also be used. A cycle is instituted by pressing the start cycle button and choosing one of the settings or operation modes via the input utility 140A, as presented by the output utility 140B of control panel 140. The output utility 140B warns the user that the sanitizing cycle is in progress (e.g., via a message on a display, or an operation of a light), and the door lock(s) (205A, 205B) engage(s) to securely lock the door(s). The control unit generates control signals to operate the fan(s) 117, the ozone generator 130, the oxygen generator 125, the one or more UV lamps (106A-C), the one or more vent locks (120A-D) if present, the door locks (205A-B) if present, and the ozone removal fan 702 and the ozone removal filter 700, if present. The control signals are sent via wiring 113 to control the operation of the fan(s) 117, the ozone generator 130, the oxygen generator 125, the one or more tJV lamps (106A-C), the one or more vent locks (120A-D) if present, and the door locks (205A-B) if present during the sanitizing cycle.

In some embodiments of the present invention, the control panel 140 is configured to receive an input from the user to interrupt a sanitizing cycle. If a sanitizing cycle is interrupted by the user, the control uit 135 causes the ozone removal filter 700 to open and the ozone removal fan 702 to drive air through the ozone removal filter 700. The door lock(s) remain engaged to keep the door(s) locked. In some embodiments of the present invention, the ozone removal fan 702 continues operating and driving air into the ozone removal filter for a predetermined time period that has been determined during the development of the assembly. At the end of the period, the ozone removal filter 700 is closed, the ozone removal fan 702 is turned off, and the door lock(s) is (are) disengaged. In some embodiments of the present invention, the ozone removal fan 702 continues operating and driving air into the ozone removal filter until the ozone level measured by the air analyzer sensor 170 falls below a predetermined safe level. When this happens, the ozone removal filter 700 is closed, the ozone removal fan 702 is turned off, and the door lock(s) is (are) disengaged.

Referring to FIG. 2, various shelves (i.e., shelves 10a-b), tiers, hooks, and other organizing means may be used to retain the items inside the cabinet 102 at a desired position during storage and sanitization. In one non-limiting embodiment, shelves 110a and 110b are high capacity shelves with a tempered glass middle. While there are two shelves in is this non-limiting embodiment, a single shelf (shelf 110A or shelf 110B) or more than two shelves may be present. Hinges 150B on door 108B and hinges on door 108A facilitate rotating movement of doors 100A-B such that doors 100A-B can be in an opened position (i.e., the cavity and contents within the cavity as described above are exposed to the ambient environment) or closed position (i.e., the cavity and contents within the cavity as described above are blocked from the ambient environment).

The ozone generator and the oxygen generator can be programmed to run simultaneously with the one or more UV lights for the predetermined time and with the open vents (i.e., the respective vents attached to vent doors 120A-C) at ceiling panel 114, fan(s) 117 at the bottom floor panel 112 aid in expelling the ozone from cabinet 102 to the ambient environment of the room. As the ozone and oxygen are expelled from cabinet 102 to the ambient environment of the room, doors 108A-B are locked and thus in closed position. Control unit 135 may send an electric command to the locks 205A and 205B (see FIG. 3) to keep doors 108A-B in the closed position during the sanitation process. In turn, the air in the ambient environment of the room is sanitized by the ozone and oxygen exhausted though the vents on the ceiling panel 114.

At the end of the sanitizing cycle the UV lamp(s), the oxygen generator and the ozone generator are switched off, the output utility of the control panel indicates that the cycle is over (e.g., cycle complete lights are turned on), and the locks of doors 108A-B are released. Cabinet 102 is now ready for unloading. At any time, a cycle in process can be cancelled by inputting a cancel command via the input utility of the control panel (e.g. by pressing the cancel button). When the cycle is cancelled to release the locks of doors 108A-B, the UV lamp(s), the oxygen generator, and the ozone generator are switched off, the output utility of the control panel indicates that the cycle is over (e.g., cycle complete lights are turned on), and the locks of doors 108A-B are released.

To further enhance the sanitizing capacity, the inner side of the walls is polished chrome to a number 8 mirror reflection, or has attached thereto a layer of reflective glass 116. In one non-limiting embodiment, the reflective glass 116 is a chrome interior polished to a number 8 mirror finish which reflects UV light all around the inside of cabinet 102. This enhances the effects of UV light inside cabinet 102 (i.e., the cavity of cabinet 102 and contents therein).

Figure 4:
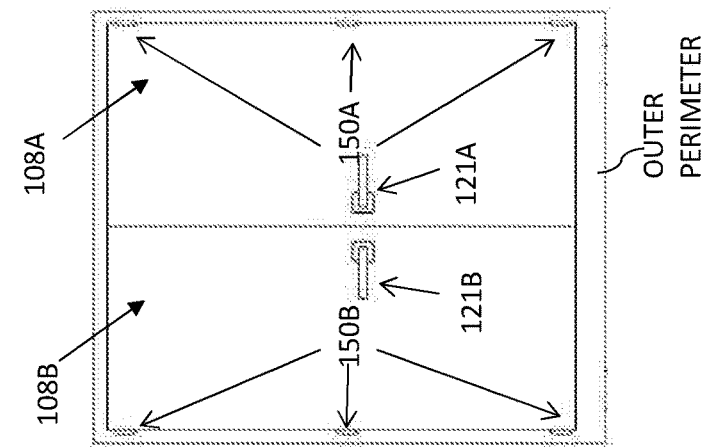
FIG. 4 is an illustration of a perspective view of the cabinet assembly, showing the doors in a closed position, in accordance with some embodiments of the present invention.
Figure 3:
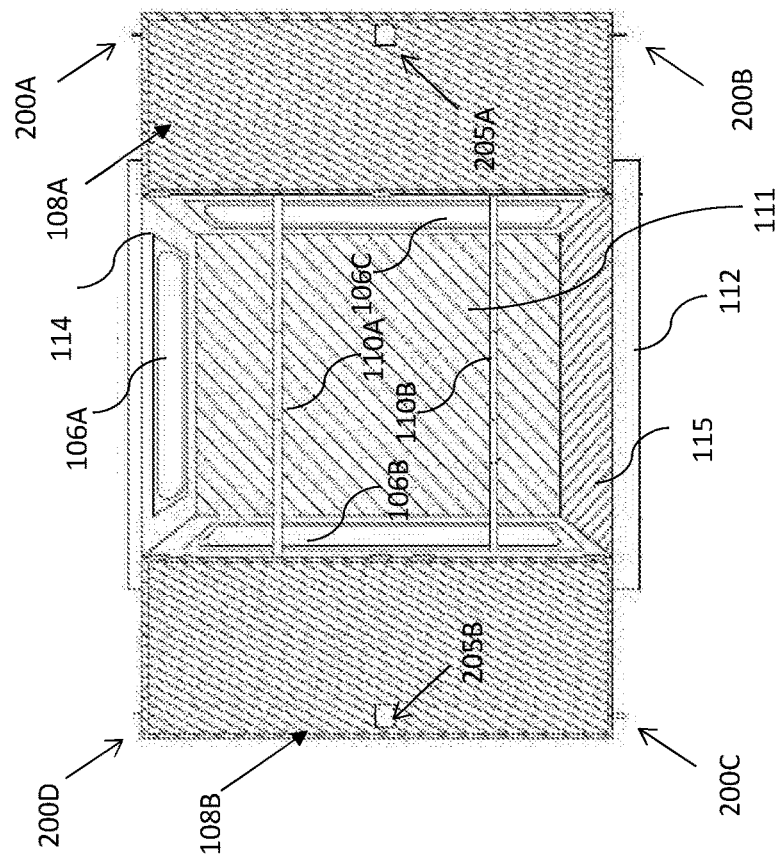
FIG. 3 is an illustration of a perspective view of cabinet assembly, showing the doors open, in accordance with some embodiments of the present invention.

Referring to FIGS. 3 and 4, an illustration of a sanitizing cabinet assembly 100 is depicted. In the example of FIG. 3, the doors 108A-B in an opened position, in accordance with an embodiment of the present invention. In the example of FIG. 3, the doors 108A-B in a closed position, in accordance with an embodiment of the present invention. The cabinet may have a height of 72 inches and a width of 36 inches, for example.

Door 108A has locking shafts 200A and/or 200B. Door 108B has locking shafts 200C and/or 200D. When engaged, locking shafts 200A-D extend away from the respective doors vertically and enter holes (not shown) in the ceiling panel 114 and on the inner floor panel 115 to prevent the doors from opening. When not engaged, the locking shafts withdraw within the respective doors to enable the doors to be opened. A locking unit 205A in door 108A controls the engagement mode of the locking shafts 200A and 200B. The locking unit 205A is attached to a handle 121A which is used by the user to lock and unlock the door 108A. Optionally, the locking unit 205A control the engagement mode of the respective locking shafts according to instructions from the control unit. Unit 205B is incorporated in door 108B and may be controlled via a handle 121B and or via instructions from the control unit. It should be noted that the locking shafts are only one non-limiting example of how doors may be locked, and any other manner of locking the door may be applied.

Back wall 111 is opposite to doors 108A-B and connects to the side walls, lower floor panel 112, and ceiling panel 114. In some embodiments of the present invention, right side wall is attached to door 108A and contains UV lamp 106C. Left side wall is attached to door 108B and contains UV lamp 106B. The ceiling panel 114 contains UV lamp 106A.

In some embodiments of the present invention, shelves 110A-B are made of a material that is transparent to UV light (e.g., tempered glass insert) such that UV light radiates to the items located on the shelves from under the shelves.

Figure 5:
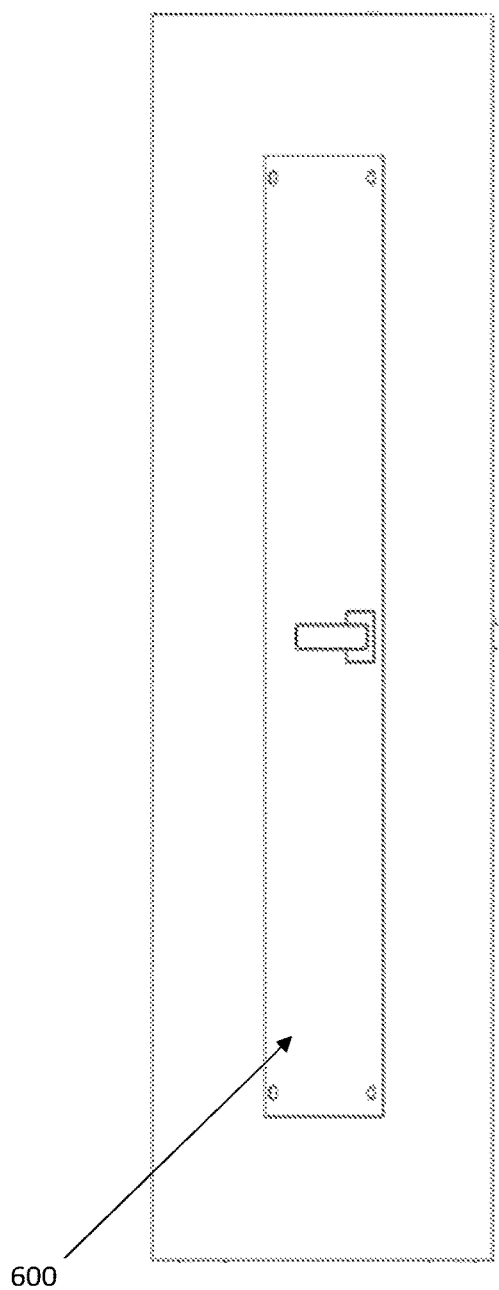
FIG. 5 is an illustration of a side view of the cabinet assembly having a side door in a closed position, in accordance with some embodiments of the present invention.
Figure 6:
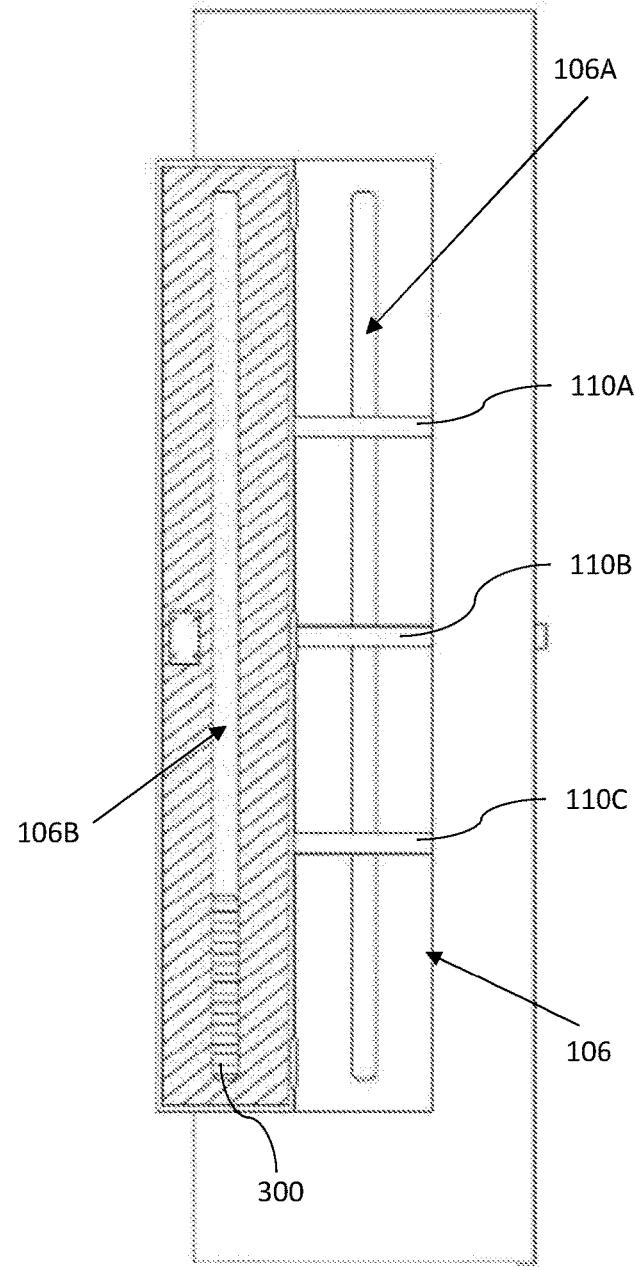
FIG. 6 is an illustration of a side view of the cabinet assembly having a side door in an open position, in accordance with some embodiments of the present invention.

Referring to FIG. 5-6, an illustration of a side view of the cabinet 100 with a side door 600 is depicted, according to some embodiments of the present invention. In FIG. 5, the side door 600 is in a closed position. In FIG. 6, the side door 600 is in an open closed position.

The side door 600 is configured for ease of access to the UV lamps. In some embodiments of the present invention, a single side door 600 is present in only one side of wall. In some embodiments of the present invention, each side wall a respective side door. The UV lamp may be joined to the inner surface of the respective side door.

Figure 10:
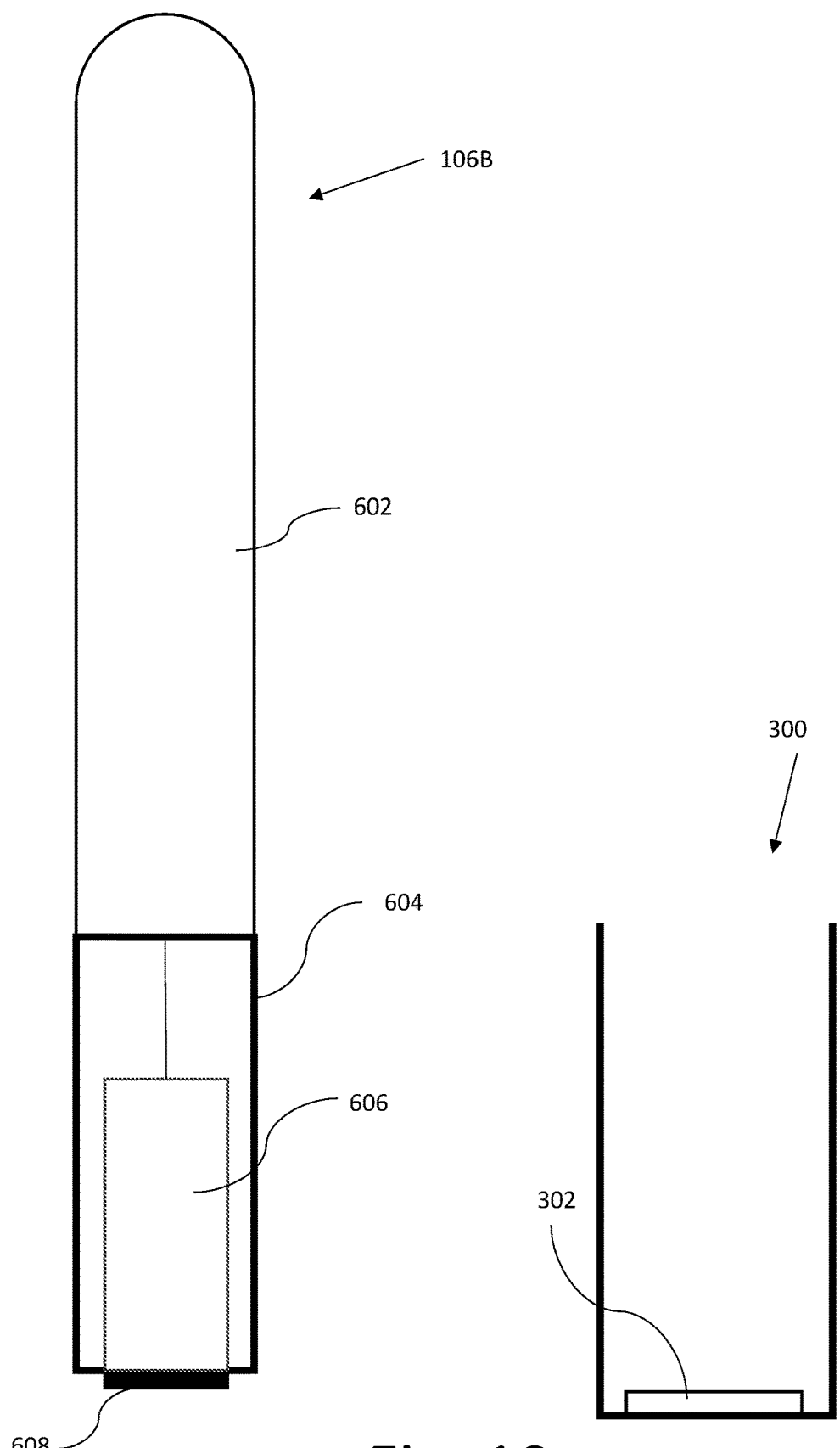
FIG. 10 is a schematic drawing illustrating a removable UV lamp removed from a holder, according to some embodiments of the present invention.
Figure 11:
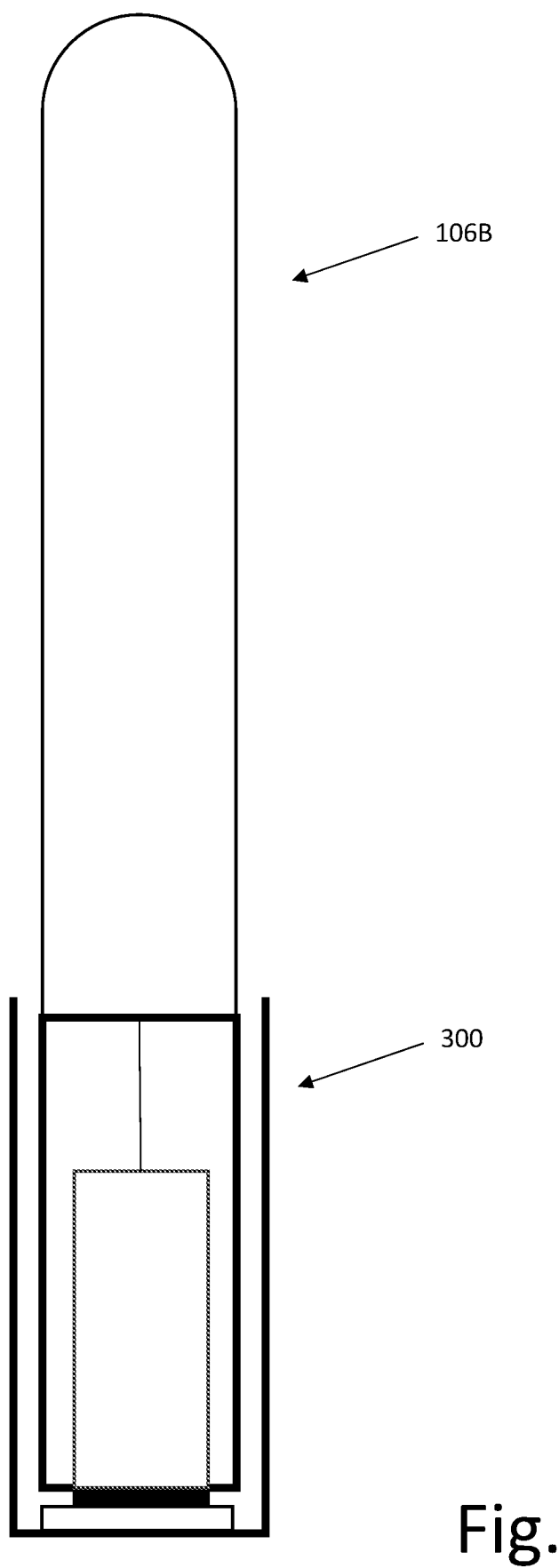
FIG. 11 is a schematic drawing illustrating a removable UV lamp joined to the holder, according to some embodiments of the present invention.

Referring to the example of FIGS. 6, 10, and 11, at least one of the UV lamps 106B is an elongated lamp. The elongated lamp may be vertically oriented. In one non-limiting embodiment, the UV lamps generate short wavelength ultraviolet (UV-C) light to kill or inactivate microorganisms by destroying nucleic acids and disrupting their DNA, generally leaving them unable to perform vital cellular functions.

In some embodiments of the present invention, at least one of the UV lamps (e.g. UV lamp 106B) on the side wall is detachable from the cabinet 102 and thereby may be used to sanitize items outside the cabinet 102. The UV lamp 106B includes a UV light source 602 joined to a handgrip 604 configured to be held by a user. The handgrip 604 also houses a rechargeable power source 606 having an extension 608 extending out of the bottom end of the handgrip 604. The rechargeable power source 606 is electrically connected to the UV light source and is configured to power the UV light source. The side door includes a holder 300 that includes a charging station 302 electrically connected to the power source of the cabinet. The holder is configured to hold the UV lamp 106B such that the charging station 302 contacts the extension 608 of the rechargeable power source 606 and charges the rechargeable power source 606, to enable to user UV lamp 106B to emit UV light while detached from the holder 300.

In some embodiments of the present invention, the holder 300 is a sleeve with the top end open, and the charging station 302 is located at the bottom inner surface of the holder 300. The extension 608 extends out of the bottom of the handgrip 604. In this manner, when the UV lamp 106B is inserted into the holder 300, the extension 608 contacts the charging station 302, as seen in FIG. 11. In some embodiments of the present invention, the sleeve is shorter than the UV lamp 106B so that when the UV lamp 106B is inserted into the sleeve, at least a majority of the light source of UV lamp 106B extends out of the sleeve. In this manner, the UV lamp efficiently illuminates the inner cavity of the cabinet when inside the sleeve. Optionally or alternatively, the sleeve is be made of a material that is transparent to UV radiation, so that UV radiation can be transmitted via the sleeve. It should be noted that the example of FIGS. 10 and 11 is non limiting, as the holder may have a different shape, the charing station 302 may be located elsewhere in the holder 300, and the extension 608 may extend from the side wall of the handgrip 604. What is important is that when the UV lamp 106B enters the holder 300, the extension 608 contacts the charging station 302, so that electrical current is transmitted from the charging station 302 to the extension 608.

Because the UV lamp 106B is removable, the UB lamp 106B may be used for killing mold in location outside the cabinet, such as air ducts and out of sight places.

Figure 7:
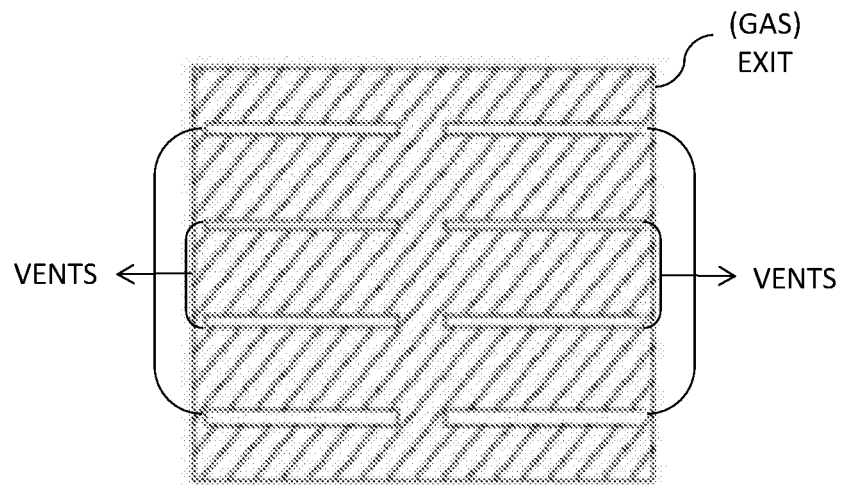
FIG. 7 is a top view of the ceiling panel of the cabinet, according to some embodiments of the present invention.

Referring to FIG. 7 and FIG. 8, assembly 100 generates oxygen and/or ozone for sanitizing the items in the cavity of the cabinet 102. The oxygen and ozone generators is designed for generation of oxygen and ozone (respectively) that efficiently kills bacteria, including: Giardia, Cryptosporidium, parasites, fungi, molds and other microbes. In one non-limiting embodiment, oxygen generator 125, ozone generator 130, and fan(s) 17 move the oxygen and ozone gases through cabinet 102 out ceiling panel 114 through the vents into the room to sanitize the air in the room cabinet 102 resides in. Apertures in lower floor panel 112 are entry points for air, wherein the air is subject to separation and purification techniques in oxygen generator 125 and ozone generator 130.

It is known in the art that the ozonation standard for killing most organisms is to maintain 0.3 ppm of ozone for a three-minute contact time. Thus, the ozone generators are programmable to generate ozone for a predetermined amount of time, or as circumstances may dictate. For example, a deep clean of a building is achieved if all the classrooms have a unit of cabinet 102 with a 3-hour preset timer activated at midnight, while the property is generally vacant.

Thus, assembly 100 is efficacious for combining UV radiation, oxygen, and ozone to sanitize objects in cabinet 102. In turn, airborne viruses and bacteria on surfaces in the room in which cabinet 102 resides in are killed.

Assembly 100 is designed for sanitizing items in a safe manner. For example, a cabinet 102, which helps reduce illness and contagious diseases by sanitizing objects that are shared by many people on a daily basis.

Thus, the ozone works to clean the air in the room where the cabinet 102 is located, plus all the surfaces visible (e.g., desks, floors, walls) and not visible (e.g., air ducts and areas behind furniture). By combining concentrated UV light to kill what it engages with and ozone to kill what the light cannot engage in a magnetically sealed unit, 99.98% of germs in the contact within cabinet 102 (internally and externally) are killed. Stated another way, the UV radiation, and generated gases provide a reinforcing technique for killing germs to achieve a sanitized state.

In a non-limiting embodiment, the construction of cabinet 102 includes manufacturing the unit with a 12 g stainless steel outer shell and a chrome interior polished to a number 8 mirror finish for reflecting the light all around. With two large doors for ease of loading by the user, a heavy weight magnetic refrigerator type door seal with a manual lock seals the doors. In some embodiments of the present invention, the doors are closed, the cabinet is hermetically closed so that air passage between the inner cavity and the outside of the cabinet occurs only via the apertures at the lower floor panel 112 and the vents at the ceiling panel 114.

Three examples of use of the cabinet can include a commercial cabinet, a school cabinet, and a household cabinet. In a commercial cabinet, a fire fighter can securely place equipment and boots into the cabinet and lock the doors. The first step in the process after equipment is placed inside the cabinet is analyzing air inside the cabinet via an air analysis sensor connected to control unit 135. Thus, control unit 135 is equipped with sensors and detectors for determining which microbes and contaminants are present. Based on the detected contaminants (if there are any), an output is presented on a screen/display of control panel 140. Control unit 135 can be equipped with an algorithm for determining what combination of UV light, ozone, and pure oxygen are needed and the amount of time the UV light, ozone, and pure oxygen needs be provided to the items therein.

In another example, a school unit in a classroom sanitizes toys and books which are shared between students. These shared toys and books can be placed in cabinet 102, where UV light is applied and ozone that can penetrate where the UV light cannot affect sanitation and thus a 99.98% level of sterilization is achieved. Further, the likelihood of children not passing viruses, bacteria, and other germs to other people is reduced or eliminated.

In another example, a parent can sterilize everything he or she feels needs sterilization in a home environment by using a household unit. Once items (e.g., toys, clothes, games and any other non-organic material) re placed in the cabinet 102 and the air within the cabinet 102 is analyzed, the control panel 140 displays a proposed mode of operation on the display. Furthermore, algorithms in proprietary software and switch board in control unit 135 and wiring 113 are used to determine how much UV light and ozone are needed to achieve the conditions for continuous sterilization in cabinet 102.

Control unit 135 and control panel 140 can be programmable devices for operating the software and electrical commands sent to locks of doors 108A-B, vent doors 120A-D, wands 106A-C, oxygen generator 125, ozone generator 130, and fan(s) 117.

The data storage utility can be a tangible device that can retain and store instructions for use by an instruction execution device. The data storage utility may be, for example, but is not limited to, an electronic storage device, a magnetic storage device, an optical storage device, an electromagnetic storage device, a semiconductor storage device, or any suitable combination of the foregoing. A non-exhaustive list of more specific examples of the data storage utility includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

Computer readable instructions described herein can be downloaded to the control unit or to an external computer or to an external storage device via a network, for example, the Internet, a local area network, a wide area network and/or a wireless network. The network may comprise copper transmission cables, optical transmission fibers, wireless transmission, routers, firewalls, switches, gateway computers, and/or edge servers.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical applications, or technical improvement over technologies found in the marketplace, or to enable others of ordinary skill in the art to understand the embodiments disclosed herein.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

What is claimed is:

1. A sanitation device, comprising:
   a hollow housing for storing one or more objects, the housing having a back wall, a front door opposite the back wall, a first side wall, a second side wall opposite the first side wall, a lower floor panel and a ceiling panel, the floor panel having an intake vent configured for intake of air from an external environment into an inner cavity of the housing, and the ceiling panel having an exhaust vent configured to exhaust air from the inner cavity of the housing to the external environment;
   at least one fan located on or near the floor panel and configured to generate an air flow from the outside environment into the inner cavity through the intake vent and back out into the outside environment via the exhaust vent;
   an ozone generator located on or near the floor panel and configured to generate ozone from at least some of the air entering via the intake vent;
   an oxygen generator located on or near the floor panel and configured to generate oxygen from at least some of the air entering via the intake vent;
   at least one ultra-violet lamp joined to at least one of the first side wall and the second side wall, and the at least one ultra-violet lamp facing the inner cavity and configured to generate ultra-violet light propagating within the inner cavity to sanitize the inner cavity;
   an air analyzer located in the inner cavity and configured to sample air in the inner cavity to identify a presence of one or more predetermined microbes and to generate data indicative of the presence of the one or more predetermined microbes;
   a control unit, configured for receiving the data from the air analyzer and to activate the at least one fan and at least one of the ozone generator, the oxygen generator, and the at least one ultra-violet lamp according to a predetermined schedule in order to kill at least a portion of the one or more predetermined microbes identified by the air analyzer.

2. The sanitation device of claim 1, comprising at least one transparent shelf configured to hold the one or more objects and allowing transmission of the ultra-violet light through the at least one transparent shelf onto the one or more objects.

3. The sanitation device of claim 1, wherein:
   the at least one ultra-violet lamp comprises a first ultra-violet lamp joined to the first side wall; and
   the first side wall comprises a first hinged side door opening outwards, the first ultra-violet lamp being joined to the first side door.

4. The sanitation device of claim 3, wherein:
   the at least one ultra-violet lamp comprises a second ultra-violet lamp joined to the second side wall; and
   the second side wall comprises a second hinged side door opening outwards, the second ultra-violet lamp being joined to the second side door.

5. The sanitation device of claim 1, wherein an inward-facing surface of the inner cavity is reflective to ultra-violet light.

6. The sanitation device of claim 1, wherein the at least one ultra-violet lamp comprises:
   a first ultra-violet lamp joined to the first side wall;
   a second ultra-violet lamp joined to the second side wall; and
   a third ultra-violet lamp joined to the ceiling panel.

7. The sanitation device of claim 1, wherein the at least one ultra-violet lamp comprises a wand which is repeatedly detachable from the hollow housing.

8. The sanitation device of claim 7, wherein the wand comprises:
   a light source, for emitting the ultra-violet light; and
   a rechargeable power source;
   wherein the hollow housing comprises a charging station configured for charging the power source when the wand is joined to the hollow housing.

9. The sanitation device of claim 1, wherein the control unit comprises a user interface configured to:
   receive an input from a user indicative of an instruction to operate at least one of the ozone generator, the oxygen generator, and the at least one ultra-violet lamp, according to an operation mode; and
   operate at least one of the ozone generator, the oxygen generator, and the at least one ultra-violet lamp, according to the input.

10. The sanitation device of claim 9, wherein the control unit comprises an output interface configured to display information showing whether the operation of the at least one of the ozone generator, the oxygen generator, and the at least one ultra-violet lamp is in progress.

11. The sanitation device of claim 9, further comprising:
    an ozone removal filter, located in the inner cavity and configured to remove ozone from air flowing therethrough; and
    an ozone removal fan, located in the inner cavity in a vicinity of the ozone removal filter and configured to drive air in the inner cavity through the ozone removal filter;
    wherein:
    the user interface is configured to receive an interruption input indicative of an instruction to interrupt the predetermined schedule;
    responsive to the interruption input, the control unit is configured to activate the ozone removal fan to drive the air in the inner cavity through the ozone removal filter.

12. The sanitation device of claim 11, wherein the control unit is configured to turn off the ozone removal fan when the control unit has determined that an ozone level in the inner cavity is below a predetermined safe level.

13. The sanitation device of claim 12, wherein the control unit is configured to determine that the ozone level in the inner cavity is below the predetermined safe level if the ozone removal fan has operated for a predetermined time period.

14. The sanitation device of claim 12, wherein:
the air analyzer is further configured to measure the ozone level in the inner cavity, to generate ozone measurement data indicative of the ozone level measured by the air analyzer, and to transmit the ozone measurement data to the control unit;
the control unit is configured to determine that the ozone level in the inner cavity is below the predetermined safe level by comparing the ozone level measured by the air analyzer to the predetermined safe level and determining that the ozone level measured by the air analyzer is below the predetermined safe level.

15. The sanitation device of claim 12, comprising:
an automatic lock on the front door, the control unit being configured to engage the automatic lock to lock the front door when the operation of the ozone generator or the oxygen generator or the at least one ultra-violet lamp is in progress and to disengage the automatic lock to unlock the front door when the operation of the ozone generator or the oxygen generator or the at least one ultra-violet lamp ends;
wherein the control unit is configured to disengage the automatic lock when the control unit has determined that the ozone level in the inner cavity is below the predetermined safe level.

16. The sanitation device of claim 11, wherein the ozone removal filter is closed and the control unit is configured to open the ozone removal filter for air to be driven through the ozone removal filter in response to the interruption input.

17. The sanitation device of claim 1, comprising an automatic lock on the front door, the control unit being configured to engage the automatic lock to lock the front door when the operation of the ozone generator or the oxygen generator or the at least one ultra-violet lamp is in progress and to disengage the automatic lock to unlock the front door when the operation of the ozone generator or the oxygen generator or the at least one ultra-violet lamp ends.

18. The sanitation device of claim 1, comprising an inner floor panel located above the floor panel and having a second vent;
wherein the ozone generator and the oxygen generator are located between the inner floor panel and the lower floor panel, such that the ozone generated by the ozone generator and the oxygen generated by the oxygen generator are driven into the inner cavity via the second vent.

19. The sanitation device of claim 1, comprising at least one vent door configured to open, partially close, and entirely close the exhaust vent.

20. The sanitation device of claim 19, wherein the control unit is configured to control a position of the at least one vent door for opening, partially closing, and entirely closing of the exhaust vent.

\* \* \* \* \*